United States Patent
Muzzolini

(10) Patent No.: US 7,526,956 B2
(45) Date of Patent: May 5, 2009

(54) MEASURING DEVICE FOR MEASURING THE HUMIDITY OF MATERIALS, PARTICULARLY TEXTILES

(75) Inventor: Dario Muzzolini, Magnano in Riviera (IT)

(73) Assignee: Electrolux Home Products Corporation N.V., Zaventem (BE)

( * ) Notice: Subject to any disclaimer, the term of this patent is extended or adjusted under 35 U.S.C. 154(b) by 416 days.

(21) Appl. No.: 11/415,629

(22) Filed: May 2, 2006

(65) Prior Publication Data

US 2006/0260394 A1    Nov. 23, 2006

(30) Foreign Application Priority Data

May 9, 2005    (EP)    ................................. 05103813

(51) Int. Cl.
*G01N 27/12*    (2006.01)
(52) U.S. Cl. .................................. 73/335.02
(58) Field of Classification Search ............. 73/335.02, 73/73
See application file for complete search history.

(56) References Cited

U.S. PATENT DOCUMENTS

| | | | | |
|---|---|---|---|---|
| 2,217,220 | A * | 10/1940 | Floyd | 324/123 R |
| 3,032,729 | A * | 5/1962 | Fluegel | 336/84 R |
| 3,167,734 | A * | 1/1965 | Brucken et al. | 338/35 |
| 3,203,107 | A | 8/1965 | Scofield | |
| 3,286,363 | A * | 11/1966 | Grimshaw | 34/546 |
| 3,287,817 | A | 11/1966 | Smith | |
| 3,445,676 | A * | 5/1969 | Kahale et al. | 307/328 |
| 3,595,070 | A * | 7/1971 | Smith | 73/73 |
| 3,822,482 | A * | 7/1974 | Cotton | 34/528 |
| 3,824,477 | A * | 7/1974 | Cotton | 327/509 |
| 2005/0150740 | A1* | 7/2005 | Finkenzeller et al. | 194/207 |

FOREIGN PATENT DOCUMENTS

| | | |
|---|---|---|
| DE | 3720164 A1 | 12/1987 |
| EP | 0565976 A1 | 10/1993 |
| FR | 2399019 A | 2/1979 |

OTHER PUBLICATIONS

European Search Report for EP 05103813, dated Dec. 12, 2005.

* cited by examiner

*Primary Examiner*—Hezron Williams
*Assistant Examiner*—Rodney T Frank
(74) *Attorney, Agent, or Firm*—Pearne & Gordon LLP

(57) ABSTRACT

The present invention relates to a measuring device for measuring the humidity of materials, in particular the humidity of textiles.

The measuring device according to the invention comprises an evaluation circuit EC having electrical terminals (8, 9), an oscillatory circuit (5) and a primary electrical circuit (1) contactlessly coupled to a secondary electrical circuit (2). Each of said primary and secondary circuit (1, 2) comprises a ferromagnetic element (3, 6) and a coil (4, 7) wrapped around it. Switching means (10) are provided for short-circuiting the coil in the secondary circuit (2) in response to the electrical resistance of an electric load connected the electrical terminals (8, 9) and output means (11) for outputting signals in response to the short-circuiting of the switching means (10) are also provided. A laundry drying machine comprising a measuring device is also disclosed.

8 Claims, 5 Drawing Sheets

MEASURING DEVICE FOR MEASURING THE HUMIDITY OF MATERIALS, PARTICULARLY TEXTILES

The present invention relates to a measuring device for measuring the humidity of materials, in particular the humidity of textiles. The materials may be in a electrically conductive container as is the case, for example, with a laundry dryer.

A measuring device is already known, wherein the specific electrical conductivity of the textiles is measured depending on the humidity. When this device is applied in a rotating drum of a dryer, sliding electrical contacts are necessary for contacting the wet laundry. Therefore such known device generally comprises a first and a second brush electrically connected to an electronic evaluation circuit able to process the signals provided by the brushes to give an indication of the laundry humidity level inside the dryer drum. The first brush is positioned in slidable contact with a first half of the dryer drum and the second brush is positioned in slidable contact with the drum spindle. The two halves of the drum are made in a conductive material and are separated by an insulating strip made, for example, of plastic material. When the drum is empty the impedance between the two halves is virtually infinite while it varies according to the laundry load, the type of fabric and the degree of the humidity when the laundry is placed in the drum.

Such known device is of relatively complicated mechanical construction and, furthermore, it has a limited reliability because of wearing of the creeping brushes. For this reason a scheduled maintenance must be supplied causing the drying machine to be undesirably stopped. In addition, an undesired noise is always caused by the brush creeping when the drying machine is working.

The aim of the present invention is therefore to solve the noted problems, eliminating the drawbacks of the cited known art and thus providing a measuring device for measuring the humidity of materials, in particular the humidity of textiles, in which mechanical contacts are eliminated.

A further purpose of the present invention is to provide a measuring device for measuring the humidity of materials that eliminates the noise production in working condition.

Another purpose of the present invention is to provide a measuring device for measuring the humidity of materials having an improved reliability, said device being simple to be made and easy to be assembled in a laundry dryer.

Advantages, objects, and features of the invention will be set forth in part in the description which follows and in part will become apparent to those having ordinary skill in the art upon examination of the following or may be learned from practice of the invention. The objects and advantages of the invention may be realised and attained as particularly pointed out in the appended claims.

The accompanying drawings, which are included to provide a further understanding of the invention and are incorporated in and constitute a part of this specification, illustrate one of the possible embodiment of the invention and together with the description serve to explain the principles of the invention.

Figure 1:
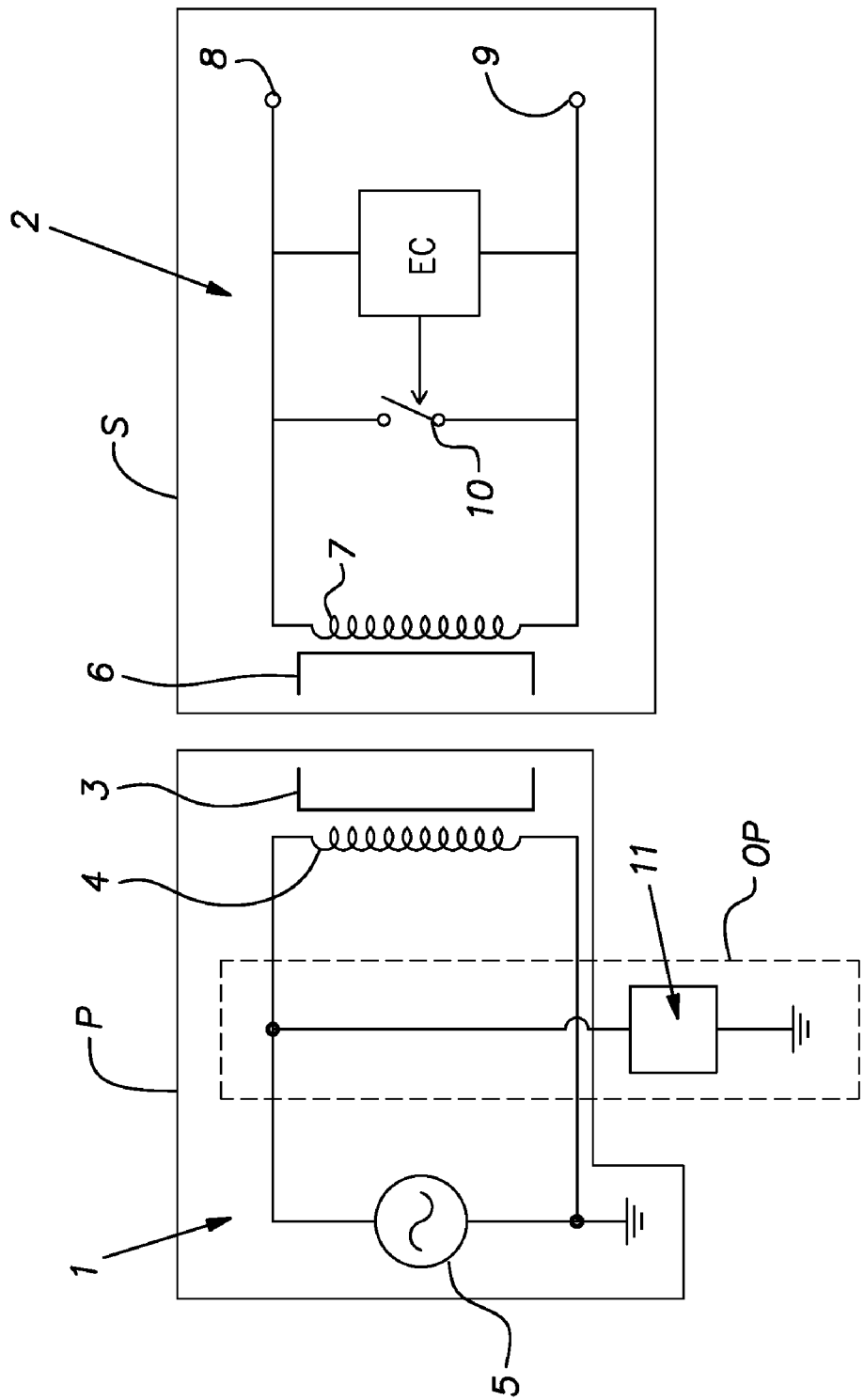
FIG. 1 shows in a schematic block diagram the circuit of a measuring device according to the invention.

With reference to FIG. 1 the measuring device according to the invention comprises a primary electrical circuit 1 shown within the closed line named "P" and a secondary electrical circuit 2 shown within the closed line named "S". Primary circuit 1 comprises a first ferromagnetic element 3 having a first coil 4 wrapped around. The coil 4 is electrically powered by an oscillatory circuit 5 able to supply an alternating voltage at a set frequency. The oscillatory circuit 5 is known per se.

The secondary circuit 2, that is physically separated from the primary circuit 1, comprises a second ferromagnetic element 6 that must be placed in a position facing the first element 3 in order to have the measuring device working correctly and efficiently. A second coil 7 is wrapped around the element 6 and it is in electrical communication with an evaluation circuit named EC having electrical terminals 8 and 9. These terminals coincide with the terminals of the secondary circuit 2.

The ferromagnetic elements 3 and 6, taken together, forms a magnetic circuit interrupted by an air gap, therefore a sort of electric transformer is formed by the elements 3 and 6 and the coils 4 and 7. The secondary circuit 2 is powered by the primary circuit 1 by means of the coupling of elements 3 and 6, while the same coupling is able to transfer a signal from the secondary circuit to the primary one as described in grater detail below.

Switching means 10 are provided in the evaluation circuit EC such that when a wet material, i.e. an electric load, is placed in contact with the terminals 8 and 9, the evaluation circuit EC causes the switching means 10 to short-circuit the second coil 7 a number of times dependent on the electrical resistence of the wet material.

The effect of the switching means 10 short-circuiting is transferred to the primary circuit 1 by means of the ferromagnetic elements 3 and 6, and output means 11 shown in the closed dashed line named OP, like for example a voltmeter, is provided for outputting signals in response to the short-circuiting of the switching means 10.

Data processing means, not shown in FIG. 1, can be provided in order to convert the output emitted by the output means 11 in a parameter indicative of the material humidity degree. Such parameter can be, for example, the time between two subsequent impulse signals output by the output means 11 and corresponding to the short-circuiting effect from the secondary to the primary circuit.

Figure 5:
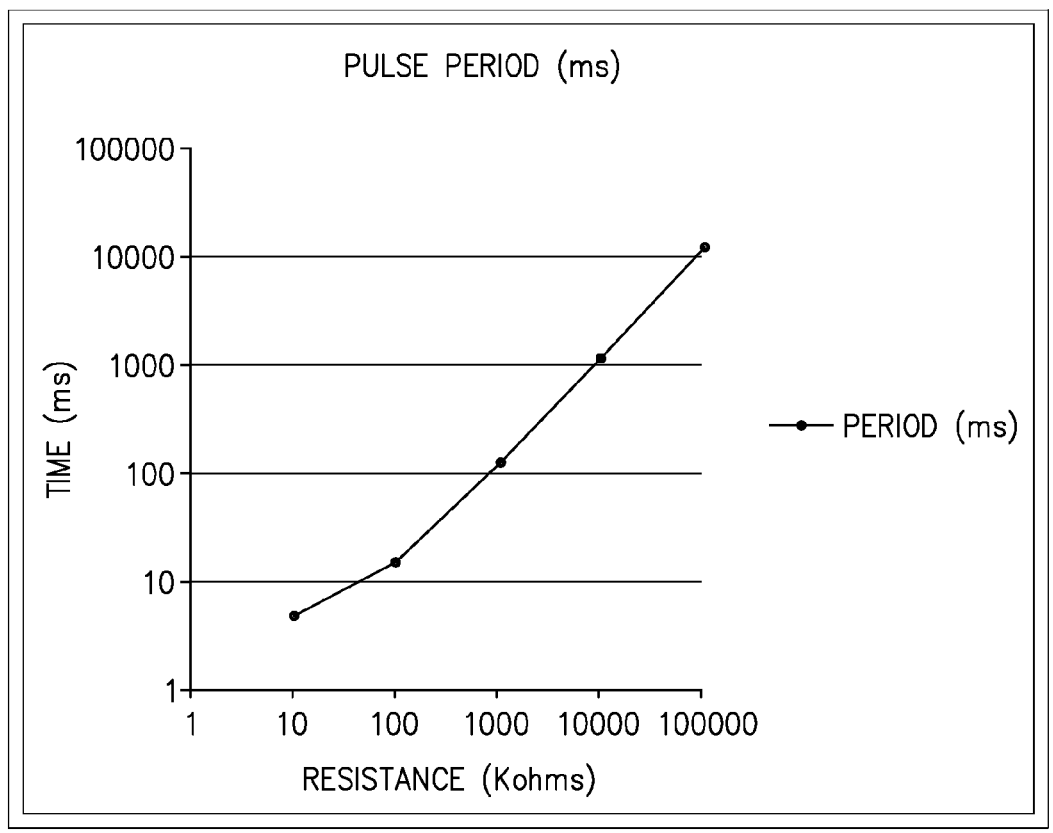
FIG. 5 shows, in a logarithmic scale, the trend of the time between two subsequent impulse signals output by the output means in response to a variable electrical resistance of a wet material.

In FIG. 5 it is illustrated the variation of the time between two subsequent impulse signals output by the output means 11 in response to a variable electrical resistance of a wet material. In the graphic time T is shown in a logarithmic scale. Said time, named T, can be calculated with the following relation when the electrical resistance $R_x$ is known: $T=1.2*10^{-7}*(30*10^4+R_x)$.

Figure 2:
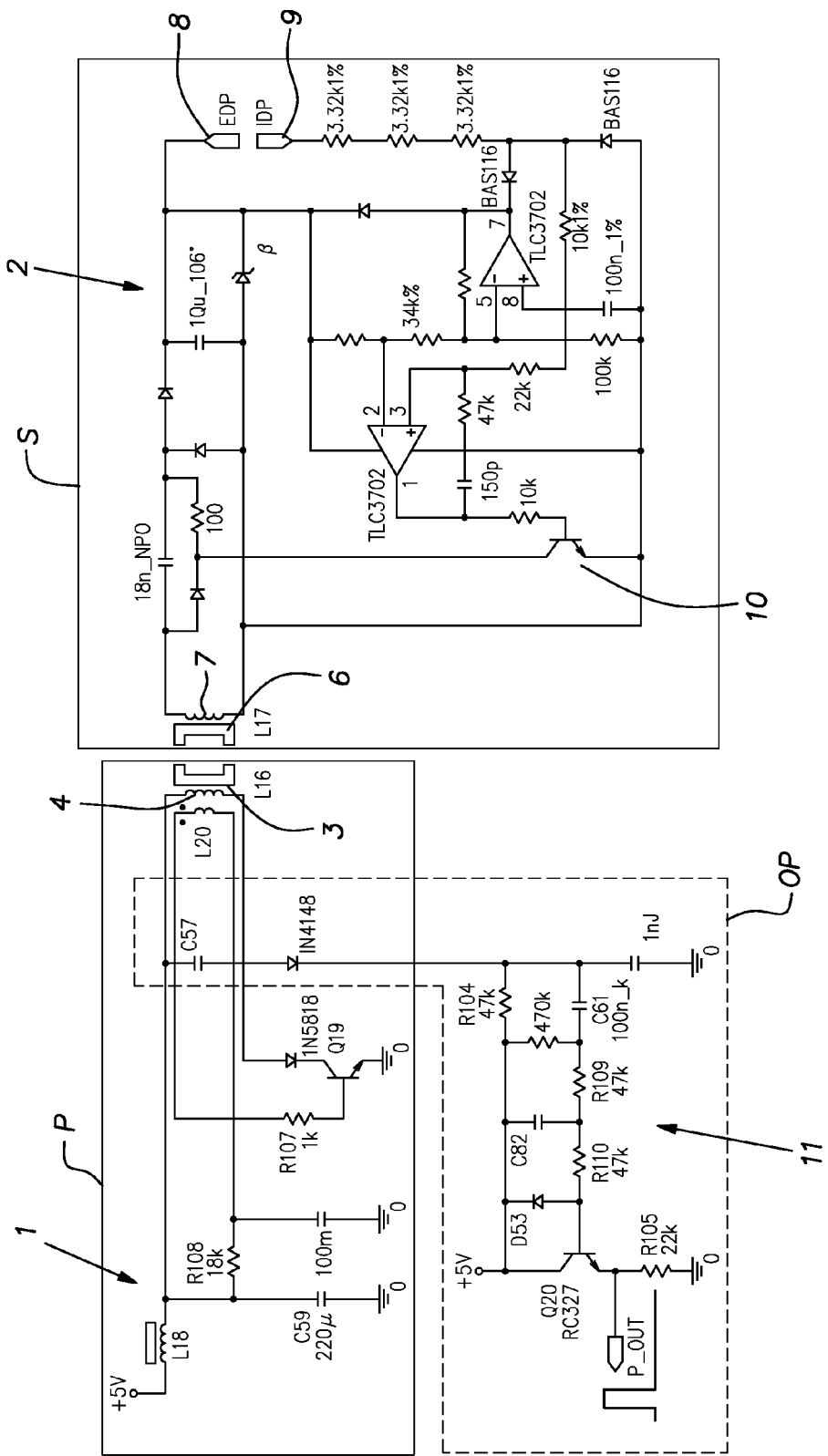
FIG. 2 shows an electronic circuit corresponding to the circuit of FIG. 1.

A detailed embodiment of the electrical circuits of the measuring device according to the invention is shown in FIG. 2. Electrical components corresponding to those shown in the schematic block diagram of FIG. 1 have been numbered correspondingly in FIG. 2.

As mentioned above, primary and secondary circuits 1 and 2 are physically separated and but in electro-magnetical communication thanks to the provision of ferromagnetic elements 3, 6 and coils 4, 7. This configuration allows to make a material humidity measurement even if this material is in motion. This is the case of wet laundry placed in a drying machine rotatable drum.

Figure 3:
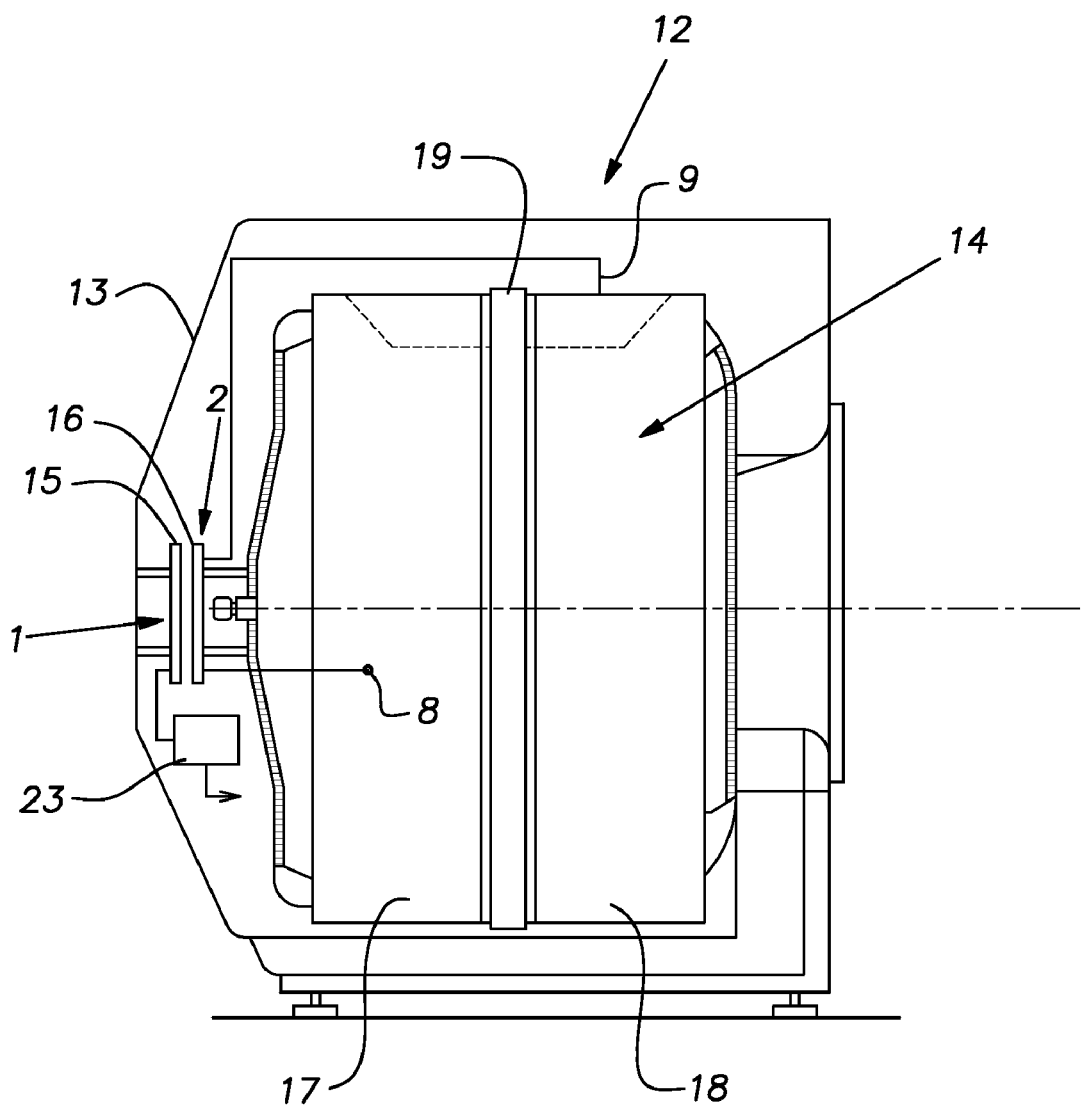
FIG. 3 shows a laundry drying machine comprising the humidity degree measuring device.

In FIG. 3 is shown a laundry drying machine 12 comprising the humidity measuring device described above. The dryer 12 comprises a main structure 13 forming the machine containing body. The primary circuit 1 of the measuring device is stably fixed on the main structure 13 by means of a first board 15. The secondary circuit 2 is carried by a second board 16 mounted on the rotatable drying drum 14 and rotating together with the latter. Said drum 14 is formed by two joined halves 17, 18 made of an electrically conductive material, and by an electrically insulating strip 19 interposed between the halves such that the latter are insulated from each other. Each electrical terminal 8 and 9 is connected to one half of the drum 14 such that a current can flow between the terminals 8 and 9 passing through the laundry contained in the drum 14.

The humidity degree of the laundry is measured by the measuring device in the above described manner. Since the laundry is progressively dried by the drying machine, its electrical resistance will change typically from a value of about 10 kohm, corresponding to laundry having a humidity grater than 20% of laundry weight (laundry completely wet), to a value of about 100 Mohm corresponding to laundry having a humidity lower than 2% of laundry weight (laundry completely dried). A trend of the time measured between two subsequent impulse signals output by the output means 11 in response to the progressively changing electrical resistance of wet laundry to be dried is shown in FIG. 5.

The humidity measurement can be carried out even when the drying machine is working, i.e. when the drum is in motion, without the need of sliding electrical contacts.

Ferromagnetic elements 3 and 6 of the primary and secondary circuits 1 and 2 are provided respectively on the boards 15, 16 such that they are facing each other.

Figure 4:
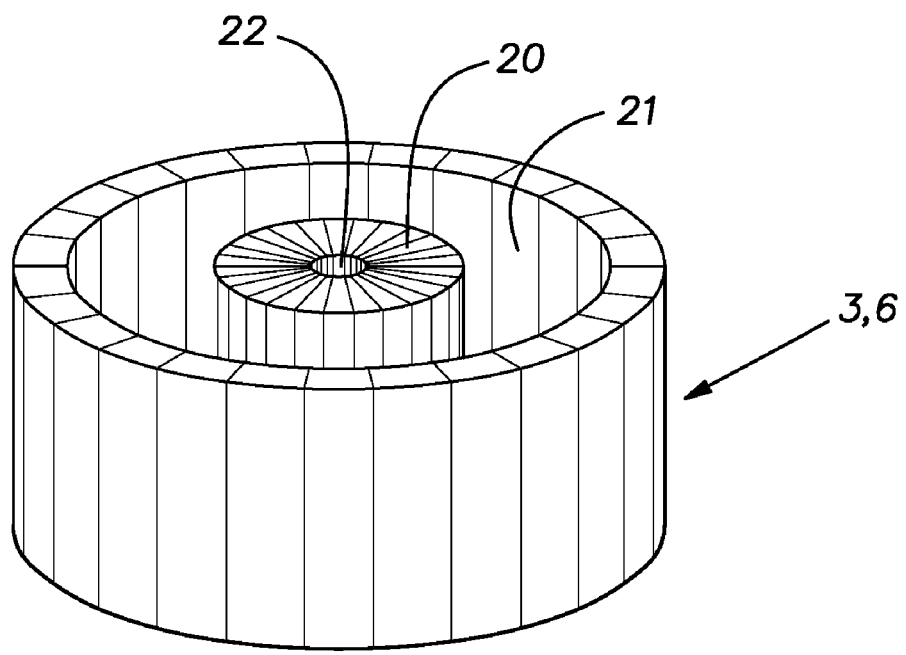
FIG. 4 shows an embodiment of the ferromagnetic element incorporating a coil.
Figure 4:
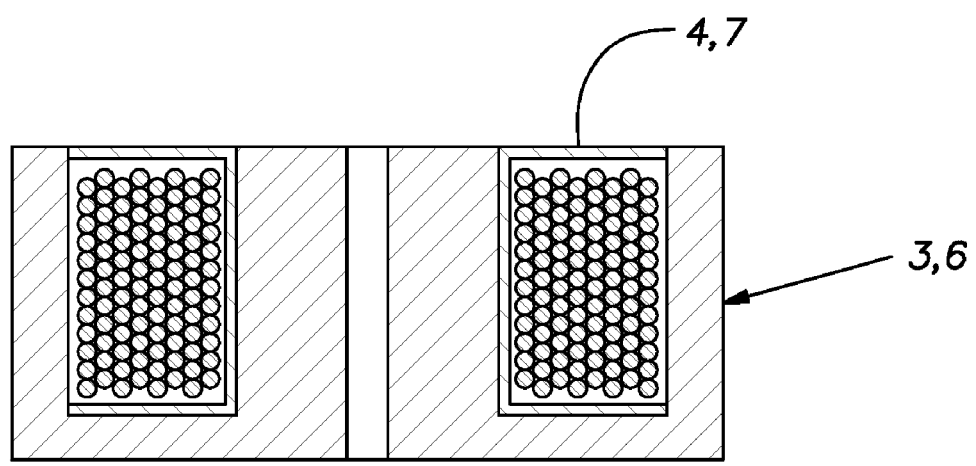

Since the element 6 rotates with the drum 14, it is important to ensure a correct match of the ferromagnetic elements independently of their reciprocal orientation. This is obtained forming the elements 3 and 6 with a cylindrical shape and providing them with a central core 20 and with an annular groove 21. A ferromagnetic element so formed is shown in FIG. 4. Each coil 4, 7 is placed within the groove 21 and wrapped around the cylindrical outer surface of the core 20. The core 20 has a through hole 22 disposed along the longitudinal axis of the element 3, 6 for mounting the latter on a support structure not shown in FIG. 4.

The output emitted by the output means 11 connected with the fixed board 15 can be sent to a drying machine programming unit by means of a electrical connection for influencing the machine working parameters according to the measured laundry degree of humidity. Said unit 23 can process the output adjusting the duration of the drying cycle and/or the heating intensity depending on the actual value of the laundry humidity.

As the present invention may be embodied in several forms without departing from the spirit or essential characteristics thereof, it should also be understood that the above-described embodiment is not limited by any of the details of the foregoing description, but rather should be construed broadly within its spirit and scope as defined in the appended claims, and therefore all changes and modifications that fall within the meets and bounds of the claims, or equivalence of such meets and bounds are therefore intended to be embraced by the appended claims.

The invention claimed is:

1. A measuring device for measuring the humidity of materials, particularly textiles, comprising an evaluation circuit EC having electrical terminals (8, 9) connectable to an electric load, and an oscillatory circuit (5), and comprising:
   a primary electrical circuit (1) comprising a first ferromagnetic element (3) having a first electric coil (4) wrapped around, said first coil being electrically powered by said oscillatory circuit (5);
   a secondary electrical circuit (2) comprising a second ferromagnetic element (6), contactlessly facing the first ferromagnetic element, having a second electric coil (7) wrapped around, said second coil (7) being in electrical communication with said evaluation circuit EC, at least one of said first and second ferromagnetic elements (3, 6) being rotatable with respect to the other;
   switching means (10), provided in said evaluation circuit EC, for intermittently short-circuiting the second coil (7) a number of times dependent on the electrical resistance of the electric load connected to the electrical terminals (8, 9);
   output means (11) for outputting signals in response to the short-circuiting frequency of the switching means (10).

2. A measuring device according to claim 1 further comprising data processing means adapted to convert the output of said output means (11) in a parameter indicative of the humidity degree.

3. A measuring device according to claim 2 wherein said parameter is a time comprised between two subsequent impulse signals emitted by said output means (11).

4. A measuring device according to claim 1 wherein the output means (11) are provided in the primary circuit (1).

5. A measuring device according to claim 1 wherein each of said first and second ferromagnetic elements (3, 6) have a cylindrical shape and are provided with a central core (20) and an annular groove (21) for receiving one of said first and second coil (4, 7) wrapped around said core (20).

6. A laundry drying machine including the measuring device of claim 1 further comprising a main structure (13) carrying the primary circuit (i) and a drum (14) adapted to receive laundry to be dried and able to rotate in respect to said structure (13), the drum being formed by two joined halves (17, 18), made of electrically conductive material, and an electrically insulating strip (19) interposed between the halves (17, 18), the drum (14) comprising a board (16) stably fixed on it and incorporating the secondary circuit.

7. A laundry drying machine according to claim 6 wherein each drum halves (17, 18) is connected with one of said electrical terminals (8, 9).

8. A laundry drying machine according to claim 6 or 7 wherein the output means (11) are electrically connected to a drying machine programming unit (23) for influencing the drying machine working parameters according to the laundry degree of humidity.

* * * * *